United States Patent
Griese et al.

(10) Patent No.: US 8,901,056 B2
(45) Date of Patent: Dec. 2, 2014

(54) REDUCING VISCOSITY UTILIZING GLYCERIN SHORT-CHAIN ALIPHATIC ETHER COMPOUNDS

(75) Inventors: Gregory G. Griese, Hudson, WI (US); Mark D. Levitt, Lake Elmo, MN (US); Carter M. Silvernail, Burnsville, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 13/484,694

(22) Filed: May 31, 2012

(65) Prior Publication Data

US 2012/0309849 A1    Dec. 6, 2012

Related U.S. Application Data

(60) Provisional application No. 61/492,684, filed on Jun. 2, 2011.

(51) Int. Cl.
| | | |
|---|---|---|
| C11D 3/44 | (2006.01) | |
| C09D 11/328 | (2014.01) | |
| C11D 7/50 | (2006.01) | |
| C11D 3/20 | (2006.01) | |
| C11D 7/26 | (2006.01) | |
| C09D 7/00 | (2006.01) | |
| C11D 3/43 | (2006.01) | |
| C09D 11/326 | (2014.01) | |
| A01N 25/02 | (2006.01) | |

(52) U.S. Cl.
CPC ............... *C11D 3/43* (2013.01); *C09D 11/328* (2013.01); *C11D 7/5022* (2013.01); *C11D 3/2068* (2013.01); *C11D 7/263* (2013.01); *C09D 7/001* (2013.01); *C09D 11/326* (2013.01); *A01N 25/02* (2013.01)
USPC ............ 510/182; 510/181; 510/342; 510/432

(58) Field of Classification Search
USPC ................... 510/181, 182, 342, 432
See application file for complete search history.

(56) References Cited

U.S. PATENT DOCUMENTS

| | | | |
|---|---|---|---|
| 3,931,033 A * | 1/1976 | Lohr et al. ................ | 510/422 |
| 5,080,822 A | 1/1992 | VanEenam | |
| 5,080,831 A | 1/1992 | VanEenam | |
| 5,158,710 A | 10/1992 | VanEenam | |
| 5,177,673 A * | 1/1993 | Nagara et al. ................ | 361/527 |
| 5,419,848 A | 5/1995 | VanEenam | |
| 5,476,971 A | 12/1995 | Gupta | |
| 5,578,090 A | 11/1996 | Bradin | |
| 5,585,341 A | 12/1996 | Van Eenam | |
| 5,661,119 A | 8/1997 | Hersh et al. | |
| 5,849,682 A | 12/1998 | Van Eenam | |
| 6,010,995 A | 1/2000 | Van Eenam | |
| 6,015,440 A | 1/2000 | Noureddini | |
| 6,083,493 A * | 7/2000 | Swaile ..................... | 424/65 |
| 6,221,816 B1 | 4/2001 | Kasuga et al. | |
| 7,098,181 B2 | 8/2006 | Inoue et al. | |
| 7,368,419 B2 | 5/2008 | Boehme et al. | |
| 7,705,069 B2 | 4/2010 | Reinhardt et al. | |
| 7,985,724 B2 | 7/2011 | Inoue et al. | |
| 8,048,840 B2 | 11/2011 | Kotera et al. | |
| 2003/0044366 A1 * | 3/2003 | Dole et al. ................ | 424/63 |
| 2005/0245411 A1 * | 11/2005 | Yang et al. ................ | 510/184 |
| 2006/0024339 A1 * | 2/2006 | Murad ................ | 424/401 |
| 2007/0269752 A1 * | 11/2007 | Lee et al. ................ | 430/418 |
| 2008/0132439 A1 | 6/2008 | Itoi et al. | |
| 2009/0197793 A1 | 8/2009 | Inoue et al. | |
| 2009/0274839 A1 * | 11/2009 | Nakata et al. ................ | 427/256 |
| 2010/0222603 A1 | 9/2010 | Selifonov | |
| 2010/0234646 A1 | 9/2010 | Nagasawa et al. | |

FOREIGN PATENT DOCUMENTS

| | | |
|---|---|---|
| JP | A 7-003289 | 1/1995 |
| JP | A-11-189796 | 7/1999 |

OTHER PUBLICATIONS

Baer, E. et al., "Naturally Occurring Glycerol Ethers III. Selachyl Alcohol and Its Geometrical Isomer", *The Journal of Biological Chemistry* 1947, 337-342.

Queste, S. et al., "Short chain glycerol 1-monoethers—a new class of green solvo-surfactants", *Green Chem.* 2006, 8, 822-830.

Queste, S. et al., "Thermophysical and bionotox properties of solvo-surfactants based on ethylene oxide, propylene oxide and glycerol", *Green Chem.* 2007, 9, 491-499.

Gu, Y. et al., "Heterogeneously catalyzed etherification of glycerol: new pathways for transformation of glycerol to more valuable chemicals", *Green Chem.* 2008, 10, 164-167.

Gu, Y. et al., "Heterogeneously catalyzed etherification of glycerol: new pathways for transformation of glycerol to more valuable chemicals", *Electronic Supplementary Information.*

Garcia, J. et al., "Green solvents from glycerol. Synthesis and physicchemical properties of alkyl glycerol ethers", *Green Chem.* 2010, 12, 426-434.

Queste, S. et al., "Hard Surface Cleaning with Solvo-Surfactants. Comparison Between Glycol and Glycerol Ethers", *Jornadas—Comite Espanol De La Detergencia*, 2006, vol. 36, 117-134.

\* cited by examiner

*Primary Examiner* — Charles Boyer
(74) *Attorney, Agent, or Firm* — IPLM Group, P.A.

(57) ABSTRACT

A solvent or composition that includes a glycerin short-chain aliphatic ether may be used in a method for coupling, coalescing or adjusting viscosity of a composition.

11 Claims, No Drawings

REDUCING VISCOSITY UTILIZING GLYCERIN SHORT-CHAIN ALIPHATIC ETHER COMPOUNDS

CROSS-REFERENCE TO RELATED APPLICATION

This application claims priority from U.S. Provisional Application Ser. No. 61/492,684, filed Jun. 2, 2011, entitled, USE OF GLYCERIN SHORT-CHAIN ALIPHATIC ETHER COMPOUNDS, the disclosure of which is incorporated by reference.

TECHNICAL FIELD

This invention relates to solvent compositions that can be used, for example, to clean, to reduce the microbial population of, to degrease, to strip floor finishes or other coatings from surfaces, to solubilize otherwise incompatible materials, to facilitate film formation of a coating, or to adjust viscosity of a composition.

BACKGROUND

Many concentrates and ready-to-use compositions have been proposed for cleaning, degreasing, stripping, disinfecting, coupling, coalescing or adjusting viscosity purposes. These formulas often contain various solvents. There is an unmet need, however, for hydrolytically stable solvents that use abundant, non-toxic, non-volatile, renewable raw materials.

SUMMARY OF THE INVENTION

The present invention provides, in one aspect, a method of adjusting viscosity comprising providing to a composition a viscosity adjuster wherein the viscosity adjuster is a glycerin short-chain aliphatic ether solvent. Another aspect of the invention provides a method of coupling or solubilizing otherwise incompatible components comprising providing to a composition a glycerin short-chain aliphatic ether solvent such that the composition is homogenous and stable.

DETAILED DESCRIPTION

The term "coalescent or coalescing agent" refers to a solvent that facilitates film formation.

The word "concentrate" refers to a composition intended to be diluted with water before use.

The term "coupling or coupling agent" refers to a solvent that solubilizes otherwise incompatible group of materials or components into homogenous, stable aqueous solution.

The term "emulsion" means one liquid dispersed into another immiscible liquid. A solvent-in-water emulsion has tiny droplets of the solvent dispersed throughout a water solution.

The term "hydrolytic stability" refers to the ability of a composition to withstand pH changes.

The term "microemulsion" means a stabilized emulsion in which the dispersed droplets are extremely small (<100 nm), and which is thermodynamically stable.

The term "phase" refers to a homogeneous fluid portion that is present in or that can form in a fluid system. The term "phases" refers to the presence of more than one phase in a heterogeneous fluid system.

The term "plasticizer" refers to a solvent that aids in formation of a film or coating or imparts to the film or coating other desirable characteristics such as more flexibility.

The term "pseudo-stable" refers to a composition that forms a single phase when subjected to mild mixing or other agitation and retains that single phase for a sufficient period of time so that the composition can be applied to a surface, but which will form two or more phases when left undisturbed.

The term "short-chain aliphatic" refers to alkyl, alkoxy, alkenyl, or cycloalkyl groups having $C_1$ to $C_3$ carbons.

The term "solvent" refers to an organic material or mixture of such materials suitable for cleaning, degreasing or stripping the desired surface, coupling, coalescing or adjusting viscosity.

The term "thermodynamically stable" means an emulsion that forms a single phase without any work being input and retains that single phase indefinitely.

The term "viscosity adjuster" refers to solvents or compositions suitable for adjusting, e.g., reducing, the viscosity, resulting in formulations being less viscous and more suitable for uses such as pouring, pumping, stirring or mixing.

Unless indicated otherwise, all parts and percentages are by weight.

All parts and percentages are by weight unless otherwise indicated.

Embodiments of the compositions contain glycerin short-chain aliphatic ethers or their salts as the solvents. The solvents may, for example, have the formula:

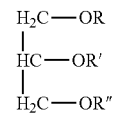

where R, R' and R" are each a short-chain aliphatic group or a hydrogen and where at least one R group is a short-chain aliphatic group.

The solvent may include any glycerin-derived short-chain aliphatic ether or salts thereof that can maintain hydrolytic stability and has low odor or low volatility (e.g. has a vapor pressure less than 0.1 mm Hg at 20° C.). In some embodiments, the short-chain aliphatic group is a methyl, ethyl, n-propyl, isopropyl or the like. The salts of the glycerin aliphatic ethers may, for example, include any halides, sodium, potassium, magnesium or calcium.

Examples of glycerin short-chain aliphatic ethers include glycerin mono methyl ether, glycerin mono ethyl ether, glycerin mono propyl ether, glycerin mono isopropyl ether or any alkoxy glycerols, alkoxy propanediols, glycerin monoethers, propanediol monoether, glycerol monoether or glyceryl ether.

The short-chain aliphatic glycerin ethers may be produced from glycerol itself or from allyl alcohols, glycidol (2,3-epoxypropyl-1propanol), or epichlorhydrin (2,3-epoxypropyl chloride). In one aspect of the invention, the glycerol is synthesized from solketal (1,2-isopropylideneglycerol) by modifying a synthesis shown in Queste et al. (Green Chem. 2006, 8, 822-830). In another aspect, the glycerin short-chain aliphatic ether is synthesized as described in Garcia et al., (Green Chem., 2010, 12:426-434) where ring opening of either glycidol ether or epichlorohydrin with corresponding alkoxide occurs in alcoholic media. Other routes of synthesis using glycerin, glycerin derivatives or other reactants could also be used.

In a diluting liquid (for example water), the solvent ranges from being totally soluble to insoluble or only sparingly soluble. Thus for compositions intended to be diluted with water, the composition may contain at least about 0.1% by weight to about 80% by weight, about 0.1% by weight to about 50% or about 0.1% to 25% by weight solvent.

The disclosed composition may, for example, contain one or more surfactants that solubilize or assist in solubilizing the solvent in a diluting liquid. The amount of surfactant may vary depending on factors such as the types and amount of other ingredients in the disclosed composition, the desired dilution level, and the intended use. As a general guide, the amount of surfactant may for example be about 0.1 to about 50%, about 0.1 to about 25% or about 0.1% to about 10% of the total concentrate weight.

Representative surfactants include water-soluble and oil-soluble anionic, cationic, amphoteric and nonionic surfactants, and mixtures thereof. Especially desirable surfactants include those that improve wetting properties of the diluted use solution, improve stability of the concentrate, or provide other desirable properties such as storage, mixing, application or stripping advantages.

Exemplary anionic surfactants include alkylbenzene sulfonates (e.g., $C_6$-$C_{24}$ alkylbenzene sulfonates), olefin sulfonates (e.g., $C_6$-$C_{24}$ olefin sulfonates), paraffin sulfonates (e.g., $C_6$-$C_{24}$ paraffin sulfonates), cumene sulfonate, xylene sulfonate, alcohol sulfates (e.g., $C_6$-$C_{24}$ or $C_6$-$C_{12}$ alcohol sulfates), alcohol ether sulfates having 1 to about 20 ethylene oxide groups, and mixtures thereof.

Exemplary cationic surfactants include quaternary amine compounds having the formula:

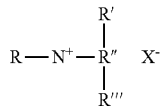

where R, R', R" and R"' are each an alkyl, aryl or aralkyl group (e.g., a $C_6$-$C_{24}$ alkyl, aryl or aralkyl group) which can optionally contain one or more P, O, S or N heteroatoms, and X is F, Cl, Br, I or an alkyl sulfate.

Exemplary amphoteric surfactants include amine oxide compounds having the formula:

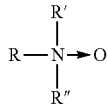

where R, R' and R" are as defined above, and mixtures thereof.

Exemplary amphoteric surfactants also include betaine compounds having the formula:

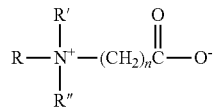

where R, R' and R" are as defined above and n is about 1 to about 10, and mixtures thereof.

Other exemplary amphoteric surfactants include imidazoline derivates including alkyl amphopropionates, alkylamphodipropionates, alkylamphoacetates and alkylamphodiacetates. Other exemplary amphoteric surfactants include alkyl aminodipropionates.

Exemplary nonionic surfactants include alcohol ethoxylates (e.g., $C_6$-$C_{24}$ or $C_6$-$C_{16}$ alcohol ethoxylates) having 1 to about 20 ethylene oxide groups (e.g., about 9 to about 20 ethylene oxide groups), alkylphenol ethoxylates (e.g., $C_6$-$C_{24}$ or $C_8$-$C_{10}$ alkylphenol ethoxylates) having 1 to about 100 ethylene oxide groups (e.g., about 12 to about 20 ethylene oxide groups), alkylpolyglycosides (e.g., $C_6$-$C_{24}$ or $C_6$-$C_{20}$ alkylpolyglycosides) having 1 to about 20 glycoside groups (e.g., about 9 to about 20 glycoside groups), and mixtures thereof.

The disclosed compositions may be formulated and sold as solvent concentrates, and may include a dilute phase liquid (e.g., water), or may be essentially anhydrous. If desired, the concentrates can be used full-strength as a cleaner, antimicrobial agent, degreaser, stripper, coupling agent, coalescing agent or a viscosity adjuster. However, the concentrates typically will be diluted with a liquid (e.g., water) that subsequently forms the dilute phase. The diluting liquid preferably is added at the time of use. A variety of dilution ratios can be employed. The ingredients in the concentrate can represent about 1 to about 99% of the diluted mixture, more preferably about 1 to about 50%, and most preferably about 1 to about 25%.

The concentrate forms a single phase before such dilution and remains so while stored in the container in which it will be sold. When combined with water or other desired diluting liquid at an appropriate dilution level and subjected to mild agitation (e.g., by stirring the composition in a bucket, pumping, spraying or using a mop, cloth or other suitable implement) some embodiments of the invention will form a pseudo-stable dispersion, and other compositions of the invention will form a clear solution or dispersion.

The disclosed compositions can contain one or more cosolvents. The cosolvent may be selected for its ability to promote formation of stable single-phase solutions, microemulsions, or dispersions.

A variety of cosolvents can be employed. In general, the cosolvent is selected based upon the characteristics of the chosen solvent and the solubility of the chosen solvent in the diluting solvent. For compositions in which water serves as the diluting solvent, the cosolvent generally will have higher water solubility than the water solubility of the chosen solvent. The cosolvent may have a high flashpoint (e.g., greater than about 50° C., more preferably greater than about 100° C., and most preferably greater than about 200° C.), low odor and low human and animal toxicity.

Examples of cosolvents include 2-(2-aminoethoxy)ethanol, monoethanolamine, diethanolamine, triethanolamine, amyl acetate, amyl alcohol, butanol, 3-butoxyethyl-2-propanol, butyl acetate, n-butyl propionate, cyclohexanone, diacetone alcohol, diethoxyethanol, diethylene glycol methyl ether, diethylene glycol n-butyl ether, diisobutyl carbinol, diisobutyl ketone, dimethyl heptanol, dipropylene glycol n-butyl ether, dipropylene glycol methyl ether, dipropylene glycol propyl ether, dipropylene glycol tert-butyl ether, ethanol, ethyl acetate, 2-ethylhexanol, ethyl propionate, ethylene glycol butyl ether, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol n-butyl ether, propylene glycol ethyl ether, propylene glycol methyl ether, propylene glycol n-propyl ether, tripropylene glycol methyl ether and tripropylene glycol n-butyl ether. Ethylene glycol butyl ether and dipropylene glycol n-butyl ether are particularly preferred cosolvents. Mixtures of cosolvents can be used if desired.

Commercially available cosolvents include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

The compositions of the invention may contain 0 to about 50 wt. % cosolvent, 0 to about 10 wt. % cosolvent, or 0 to about 5 wt. % cosolvent.

The disclosed compositions can further contain antimicrobial or biocidal agents. Suitable antimicrobial agents include carboxylic acids (e.g., butyric acid, heptanoic acid, octanoic acid, nonanoic acid, and decanoic acid), sulfonic acids (e.g., dodecylbenzene sulfonic acid), active halogen compounds (e.g., sodium hypochlorite or sodium chlorite), active oxygen compounds (e.g., hydrogen peroxide, or equilibrium derived or isolated peracids such as peracetic acid, perheptanoic acid, persulfonated oleic acid, peroctanoic acid, performic acid, percitric acid, perglycolic acid, perlactic acid, perbenzoic acid, and monoester peracids derived from diacids such as adipic, succinic, glutaric, or malonic acid and mixtures thereof), phenolic derivatives (e.g., o-phenyl phenol, o-benzyl-p-chlorophenol and tert-amyl phenol), quaternary ammonium compounds (e.g., alkyldimethylbenzyl ammonium chloride, dialkyldimethyl ammonium chloride and mixtures thereof), and mixtures of such antimicrobial or biocidal agents, in an amount sufficient to provide the desired degree of microbial protection. If present in the concentrate, the antimicrobial or biocidal agent is about 0.01 to about 70% of the concentrate, about 0.1 to about 50%, or about 0.5 to about 30%.

If desired, the disclosed solvent compositions may contain various adjuvants such as chelants, builders or fillers, thickeners, fragrances, dyes, pH adjusters, anticorrosion additives, defoamers, and antirust additives. The types and amounts of such adjuvants will be apparent to those skilled in the art.

The disclosed composition may include one or more enzymes, which can provide desirable activity for removal of protein-based, carbohydrate-based, or triglyceride-based stains from substrates; for cleaning, destaining, and sanitizing presoaks, such as presoaks for flatware, cups and bowls, and pots and pans; presoaks for medical and dental instruments; or presoaks for meat cutting equipment; for machine warewashing; for laundry and textile cleaning and destaining; for carpet cleaning and destaining; for cleaning-in-place and destaining-in-place; for cleaning and destaining food processing surfaces and equipment; for drain cleaning; presoaks for cleaning; and the like. Enzymes may act by degrading or altering one or more types of soil residues encountered on a surface or textile thus removing the soil or making the soil more removable by a surfactant or other component of the cleaning composition. Both degradation and alteration of soil residues can improve detergency by reducing the physicochemical forces which bind the soil to the surface or textile being cleaned, e.g., the soil becomes more water soluble. For example, one or more proteases can cleave complex, macromolecular protein structures present in soil residues into simpler short chain molecules which are, of themselves, more readily desorbed from surfaces, solubilized or otherwise more easily removed by detersive solutions containing said proteases.

Suitable enzymes may include a protease, an amylase, a lipase, a gluconase, a cellulase, a peroxidase, or a mixture thereof of any suitable origin, such as vegetable, animal, bacterial, fungal or yeast origin. Selections are influenced by factors such as pH-activity stability optima, thermostability or stability to active detergents, builders and the like. In this respect bacterial or fungal enzymes may be preferred, such as bacterial amylases and proteases, and fungal cellulases. Preferably the enzyme may be a protease, a lipase, an amylase, or a combination thereof. Enzyme may be present in the composition from at least 0.01 wt %, or 0.01 to 5 wt %.

The disclosed composition may further include an enzyme stabilizing system. The enzyme stabilizing system can include a boric acid salt, such as an alkali metal borate or amine (e.g. an alkanolamine) borate, or an alkali metal borate, or potassium borate. The enzyme stabilizing system can also include other ingredients to stabilize certain enzymes or to enhance or maintain the effect of the boric acid salt.

For example, a cleaning composition can include a water soluble source of calcium and/or magnesium ions. Calcium ions are generally more effective than magnesium ions and are preferred herein if only one type of cation is being used. Cleaning and/or stabilized enzyme cleaning compositions, especially liquids, may include 1 to 30, 2 to 20, or 8 to 12 millimoles of calcium ion per liter of finished composition, though variation is possible depending on factors including the multiplicity, type and levels of enzymes incorporated. Water-soluble calcium or magnesium salts may be employed, including for example calcium chloride, calcium hydroxide, calcium formate, calcium malate, calcium maleate, calcium hydroxide and calcium acetate; more generally, calcium sulfate or magnesium salts corresponding to the listed calcium salts may be used. Further increased levels of calcium and/or magnesium may of course be useful, for example for promoting the grease-cutting action of certain types of surfactant.

Stabilizing systems of certain cleaning compositions, for example warewashing stabilized enzyme cleaning compositions, may further include 0 to 10%, or 0.01% to 6% by weight, of chlorine bleach scavengers, added to prevent chlorine bleach species present in many water supplies from attacking and inactivating the enzymes, especially under alkaline conditions. While chlorine levels in water may be small, typically in the range from about 0.5 ppm to about 1.75 ppm, the available chlorine in the total volume of water that comes in contact with the enzyme, for example during warewashing, can be relatively large; accordingly, enzyme stability to chlorine in-use can be problematic.

Suitable chlorine scavenger anions are readily available, and, if used, can be salts containing ammonium cations with sulfite, bisulfite, thiosulfite, thiosulfate, iodide, etc. Antioxidants such as carbamate, ascorbate, etc., organic amines such as ethylenediaminetetracetic acid (EDTA) or alkali metal salt thereof, monoethanolamine (MEA), and mixtures thereof can likewise be used.

The disclosed composition may include a chelating/sequestering agent such as an aminocarboxylic acid, a condensed phosphate, a phosphonate, a polyacrylate, and the like. In general, a chelating agent is a molecule capable of coordinating (e.g., binding) the metal ions commonly found in natural water to prevent the metal ions from interfering with the action of the other detersive ingredients of a cleaning composition. The chelating/sequestering agent may also function as a threshold agent when included in an effective amount. The composition may include 0.1-70 wt %, or 5-60 wt %, of a chelating/sequestering agent. An iminodisuccinate (available commercially from Bayer as IDS™.) may be used as a chelating agent.

Useful aminocarboxylic acids include, for example, N-hydroxyethyliminodiacetic acid, nitrilotriacetic acid (NTA), ethylenediaminetetraacetic acid (EDTA), N-hydroxyethylethylenediaminetriacetic acid (HEDTA), diethylenetriaminepentaacetic acid (DTPA), and the like.

Examples of condensed phosphates useful in the disclosed composition include sodium and potassium orthophosphate, sodium and potassium pyrophosphate, sodium tripolyphosphate, sodium hexametaphosphate, and the like.

The composition may include a phosphonate such as 1-hydroxyethane-1,1-diphosphonic acid and the like.

Polymeric polycarboxylates may also be included in the composition. Those suitable for use as cleaning agents have pendant carboxylate groups and include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

Bleaching agents for lightening or whitening a substrate, include bleaching compounds capable of liberating an active halogen species, such as $Cl_2$, $Br_2$, $-OCl^-$ or $-OBr^-$, under conditions typically encountered during the cleansing process. Suitable bleaching agents include, for example, chlorine-containing compounds such as a chlorine, a hypochlorite, chloramines, and the like. Halogen-releasing compounds may include the alkali metal dichloroisocyanurates, chlorinated trisodium phosphate, the alkali metal hypochlorites, monochloramine and dichloramine, and the like. Encapsulated chlorine sources may also be used to enhance the stability of the chlorine source in the composition.

A bleaching agent may also be a peroxygen or active oxygen source such as hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like. A cleaning composition may include a minor but effective amount of a bleaching agent, such as 0.1-10 wt %, or 1-6 wt %.

A disclosed composition may include a minor but effective amount of one or more of a detergent filler or builder which does not perform as a cleaning agent per se, but cooperates with the cleaning agent to enhance the overall cleaning capacity of the composition. Examples of fillers suitable for use in the present cleaning compositions include sodium sulfate, sodium chloride, starch, sugars, $C_1$-$C_{10}$ alkylene glycols such as propylene glycol, and the like. Inorganic or phosphate-containing detergent builders may include alkali metal, ammonium and alkanolammonium salts of polyphosphates (e.g. tripolyphosphates, pyrophosphates, and glassy polymeric meta-phosphates). Non-phosphate builders may also be used. A detergent filleror builider may be included in an amount of 1-20 wt %, or 3-15 wt %.

A minor but effective amount of a defoaming agent for reducing the stability of foam may also be included in the compositions. Examples of defoaming agents include silicone compounds such as silica dispersed in polydimethylsiloxane, fatty amides, hydrocarbon waxes, fatty acids, fatty esters, fatty alcohols, fatty acid soaps, ethoxylates, mineral oils, polyethylene glycol esters, alkyl phosphate esters such as monostearyl phosphate, and the like. The cleaning composition can include 0.01-5 wt % of a defoaming agent, or 0.01-3 wt %.

The disclosed composition may include an anti-redeposition agent capable of facilitating sustained suspension of soils in a cleaning solution and preventing the removed soils from being redeposited onto the substrate being cleaned. Examples of suitable anti-redeposition agents include fatty acid amides, fluorocarbon surfactants, complex phosphate esters, styrene maleic anhydride copolymers, and cellulosic derivatives such as hydroxyethyl cellulose, hydroxypropyl cellulose, and the like. The composition may include 0.5-10 wt %, or 1-5 wt %, of an anti-redeposition agent.

Various dyes, odorants including perfumes, and other aesthetic enhancing agents may also be included in the composition. Dyes may be included to alter the appearance of the composition, as for example, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like.

Fragrances or perfumes that may be included in the compositions include, for example, terpenoids such as citronellol, aldehydes such as amyl cinnamaldehyde, a jasmine such as CIS-jasmine or jasmal, vanillin, and the like.

An alkalinity source or an acidic source may be provided to adjust the pH of composition. Exemplary alkalinity sources include an alkali metal silicate, hydroxide, phosphate, or carbonate.

The alkalinity source can include an alkali metal hydroxide including sodium hydroxide, potassium hydroxide, lithium hydroxide, etc. Mixtures of these hydroxide species can also be used. Alkaline metal silicates can also act as a source of alkalinity for the detergents of the invention.

The alkalinity source can include an alkali metal carbonate. Alkali metal carbonates which may be used include sodium carbonate, potassium carbonate, sodium or potassium bicarbonate or sesquicarbonate, among others. These sources of alkalinity can be used in the disclosed composition at concentrations of 0.1 wt-% to 70 wt-%, 1 wt-% to 30 wt-%, or 5 wt-% to 20 wt-%.

The divalent ion can be, for example, calcium or magnesium. The calcium ions can, for example, be added as a chloride, hydroxide, oxide, formate, acetate, nitrate salt. The disclosed compositions may contain a divalent ion, selected from calcium and magnesium ions, at a level of from 0.05% to 5% by weight, or from 0.1% to 1% by weight, or 0.25% by weight of the composition.

The acidic source or acidulants may include an acid which may be common commercially-available weak inorganic and organic acids. Useful weak inorganic acids include phosphoric acid and sulfamic acid. Useful weak organic acids include acetic acid, hydroxyacetic acid, citric acid, tartaric acid and the like. Acidulants found useful include organic and inorganic acids such as citric acid, lactic acid, acetic acid, glycolic acid, adipic acid, tartaric acid, succinic acid, propionic acid, maleic acid, alkane sulfonic acids, cycloalkane sulfonic acids, as well as phosphoric acid and the like or mixtures thereof.

The disclosed compositions may also contain additional typically nonactive materials, with respect to cleaning properties, generally found in liquid pretreatment or detergent compositions in conventional usages. These ingredients are selected to be compatible with the materials of the invention and include such materials as fabric softeners, optical brighteners, soil suspension agents, germicides, viscosity modifiers, inorganic carriers, solidifying agents and the like.

The disclosed composition can also include a polyol. The polyol may provide additional stability and hydrotrophic properties to the composition. Propylene glycol and sorbitol are examples of some polyols.

The disclosed compositions can also be used in various consumer and commercial products such as adhesives, adhesive removers, air fresheners, antiperspirants, astringents or toners, automotive polishing and cleaners, bathroom and tile cleaners, bug and tar removers, general purpose cleaners, charcoal lightener fluids, kitchen degreasers, deodorants, disinfectants, engine degreasers, fabric protectants, fabric softeners, fabric refresher, floor maintenance products, hair products, paint products, footwear or leather care products, furniture maintenance products, general purpose degreasers, insect repellents, insecticides, odor removers or eliminators, oven or grill cleaners, automotive washes, personal fragrance products, rubber/vinyl protectants, sanitizers, paint thinners, paint removers, sealants or caulking compounds, shaving creams or gels, silicone-based and multi-purpose lubricants or special-purpose lubricants, toilet cleaners, wood cleaners, and windshield water repellents to name a few.

The disclosed compositions can be applied to surfaces using a variety of methods, including spraying, brushing, wiping, mopping and flood coating. The disclosed solvent compositions can be applied to a variety of materials and to a variety of surfaces. For example, the solvent compositions can be used to remove paints, finishes, photoresists, inks, oils, food soils and other coatings from hard surfaces and soft surfaces having smooth or porous topography. Suitable hard surfaces include, for example, architectural surfaces (e.g., floors, walls, windows, sinks, tables, counters and signs); eating utensils; hard-surface medical or surgical instruments and devices; hard-surface packaging; and transportation vehicles and vehicle components (e.g., automobiles, motorcycles, bicycles, and aircraft; and wheels, gears, engines and other parts therefor). Such hard surfaces can be made from a variety of materials comprising, for example, ceramics, metals, woods or hard plastics. Suitable soft surfaces include, for example, wallpaper; carpet; soft-surface medical or surgical instruments and devices; and soft-surface packaging. Such soft surfaces can be made from a variety of materials comprising, for example, paper, fiber, woven or nonwoven fabric or soft plastics. The disclosed compositions can also be used in the laundry process as a pre-spotter or part of the main wash step. The disclosed compositions can also be applied to soft surfaces such as food substances and skin. In addition, the disclosed compositions can be used to reduce the microbial population of surfaces in areas such as kitchens, bathrooms, factories, hospitals, dental offices, food plants, and the like as well as act to aid in increasing the effectiveness of a primary antimicrobial agent. A further use of the disclosed solvent or composition is as a coating coalescing agent, a viscosity adjuster, a coupling agent or a plasticizer.

Some aspects of the solvent or composition can be used in paints to adjust the curing properties, or viscosity of the paint, or to dissolve or disperse different components in paint formulations (such as pigment and resin), making paint the desired consistency for application. Once paint is applied, the disclosed solvent evaporates, allowing resin and pigment to produce a film or a coat of paint and the paint to dry rapidly. The disclosed solvents can be used in durable and decorative coatings and paints for indoor and outdoor use, and as thinners or coalescents. The disclosed solvent or composition may be added to resin formulations such as polyamide resin. The disclosed solvent or composition may be used in aqueous coatings to aid in film formation and subsequently evaporate or may remain in the film and can potentially act as a plasticizer.

In other aspects, the disclosed composition or solvents can be used in ink-jet ink compositions to disperse colorants such as dyes pigments or combinations thereof, to prevent inter-color bleeding of the colorant. Ink jet compositions use a number of ethylene glycol derivatives to prevent inter-color bleeding. These glycols may be substituted with more environmentally preferred short-chain aliphatic ethers as disclosed. Ink-jet compositions also use anti-cockle and anti-curl agents to improve the inks' physical properties (e.g. jetting performance and the like). These agents, however, have undesirably high viscosity. Use of the disclosed composition or solvents to adjust viscosity of the anti-cockle or anti-curl agents allows for better ink-jet formulations.

Some aspects of the compositions of the invention provide pseudo-stable compositions that phase-separate following application of the composition to a surface. These compositions can also be described as exhibiting phase-splitting characteristics. Other aspects of the invention provide the compositions as a solution, dispersion, emulsion, or micro emulsion.

Aspects of the invention are further illustrated in the following non-limiting examples, in which all parts and percentages are by weight unless otherwise indicated.

Example 1

5 mol (64.3 g) of solketal, 180 mL of KOH 33% and 0.025 mol (8 g) of tetrabutylammonium bromide were successively introduced in a 1 L two-neck round bottom flask, and stirred vigorously for 15 minutes at 25° C. 0.5 Mol of bromoalkane (CiH2i+1Br) was then added drop wise. At the end of the addition, the temperature was raised to 100° C., and the mixture was stirred vigorously for 24 hours. The organic phase was then separated, dried over sodium sulfate, and distilled under reduced pressure to obtain pure alkylsolketal. The pure alkylsolketal was then added, in a 1 L round bottom flask, to 500 mL HCl (2 M). After 4 hours vigorous stirring at room temperature, the mixture was neutralized with aqueous NaOH, and extracted 3 times with 200 mL of $CH_2Cl_2$. $CH_2Cl_2$ was chosen because of its high efficiency, however, cyclohexane can also be used, as well as other "greener" solvents. The organic phases were collected, dried over sodium sulfate, and $CH_2Cl_2$ was removed under reduced pressure. Finally, the residue was distilled under vacuum and under argon to obtain pure 1-O-alkylglycerol, which was stored on molecular sieves under argon. Purity was checked by $^1H$ and $^{13}C$ NMR, and by gas chromatography.

Example 2

Laundry formulations were prepared by mixing together the ingredients in the percentage amounts shown below in Table 1:

TABLE 1

| Ingredients | Comparative Example A | Example 2A | Example 2B |
|---|---|---|---|
| Water | 70.5 | 70.4 | 68.6 |
| EDTA 40% | 3.0 | 3.0 | 3.0 |
| Dodecylbenzene sulfonic | 9.2 | 9.2 | 9.2 |

TABLE 1-continued

| Ingredients | Comparative Example A | Example 2A | Example 2B |
|---|---|---|---|
| acid, sodium salt | | | |
| Cocamidopropyl Betaine 30% | 1.3 | 1.3 | 1.25 |
| Coco diethanolamide | 0.05 | 0.05 | 0.05 |
| Sodium xylene sulfonate[1] | 6.8 | 6.8 | 6.8 |
| Ethylene Glycol Mono Butyl Ether | 4.1 | 0 | 0 |
| Glycerin Ethyl Ether | 0.0 | 4.2 | 0 |
| Glycerin Methyl Ether | 0 | 0 | 6.0 |
| Lauryl Dimethylamine Oxide 30% | 1.4 | 1.4 | 1.4 |
| Alc. Ethox. C9-11 6 EO | 0.9 | 0.92 | 0.92 |
| Alc. Ethox. C12-16 7 EO | 0.5 | 0.5 | 0.5 |
| D'Limonene | 1.2 | 1.2 | 1.2 |
| Monoethanolamine (MEA) | 1.0 | 1.0 | 1.0 |
| Water | 0.2 | 0.2 | 0.2 |
| Dye, Turquoise XB CDB | 0.003 | 0.003 | 0.003 |

[1]SXS 40% from Huntsman.

Table 1 illustrates the glycerin short-chain aliphatic ether as a coupling agent in a laundry formulation. D-limonene, while not only an expensive ingredient, is very water-insoluble. The solvent, ethylene glycol mono butyl ether helps solubilize the D-limonene. Similar results were obtained when ethylene glycol mono butyl was replaced by glycerin ethyl ether or glycerin methyl ether. Moreover, the ethylene glycol mono butyl ether, which is a volatile compound is replaced by the glycerin short-chain aliphatic ether, a non-VOC component.

Example 3

Antimicrobial formulations were prepared by mixing together the ingredients in the percentage amounts shown below in Table 2:

TABLE 2

| Ingredients | Comparative Example B | Example 3 |
|---|---|---|
| Water | 43.4 | 43.4 |
| Linear dodecylbenzene sulfonic acid | 19.2 | 19.2 |
| Dipropylene glycol methyl ether[1] | 5.0 | 0 |
| Glycerin Ethyl Ether | 0 | 5.0 |
| Propylene glycol phenyl ether[2] | 32.4 | 32.4 |

[1]DOWANOL ™ DPM from Dow Chemical Co.
[2]DOWANOL PPh from Dow Chemical Co.

Table 2 further illustrates the viscosity adjusting effect of glycerin short-chain aliphatic ethers in an antimicrobial formulation. In the comparative example, dipropylene glycol methyl ether serves as a viscosity adjuster for the formulation. When dipropylene glycol methyl ether is replaced by a glycerin short-chain aliphatic ether, the formulation continues to have a reduced viscosity.

Example 4

Antimicrobial formulations may be prepared by mixing together the ingredients in the percentage amounts shown below in Table 3:

TABLE 3

| Ingredients | Comparative Example C | Example 4 |
|---|---|---|
| Water | 33.4 | 33.4 |
| Quaternary ammonium chloride mixture[1] | 1.6 | 1.6 |
| Propylene glycol phenyl ether | 17.0 | 0 |
| Glycerin Ethyl Ether | 0 | 17.0 |
| Alcohol ethoxylate, C11, 6EO[2] | 10.0 | 10.0 |
| Octyl Amine Oxide | 30.0 | 30.0 |
| Tetrasodium ethylenediaminetetra acetate[3] | 8.0 | 8.0 |

[1]BARDAC ™ 205M from Lonza Inc.
[2]TOMADOL ™ 1-6 from Tomah Products Inc.
[3]VERSENE ™ 100 from Dow Co.

As shown in Table 3, the glycerin ethyl ether may replace propylene glycol phenyl ether (DOWANOL PPh™). The glycerin ethyl ether, similar to DOWANOL PPh™, may be able to increase the effectiveness of the antimicrobial agent.

Example 5

Glass cleaner formulations may be prepared by mixing together the ingredients in the percentage amounts shown below in Table 4:

TABLE 4

| Ingredients | Comparative Example D | Example 5 |
|---|---|---|
| Water | 97.0 | 97.0 |
| IPA | 2.0 | 2.0 |
| Hexylene Glycol | 1.0 | 0.0 |
| Glycerin Ethyl Ether | 0 | 1.0 |

As shown in Table 4, the glycerin ethyl ether replaces hexylene glycol. The glycerin ethyl ether may be able to serve as a glass cleaner similar to the comparative example D.

Example 6

Hard surface cleaner formulations were prepared by mixing together the ingredients in the percentage amounts shown below in Table 5:

TABLE 5

| Ingredients | Comparative Example E | Example 6A | Example 6B |
|---|---|---|---|
| Water | 79.7 | 79.7 | 80.7 |
| MgCl2 | 2.3 | 2.3 | 2.3 |
| Linear dodecylbenzen sulfonic acid | 7.4 | 7.4 | 7.4 |
| TEA | 1.3 | 1.3 | 1.3 |
| NaOH | 1.5 | 1.5 | 1.5 |
| Sodium laurylether sulfate 60% | 3.5 | 3.5 | 3.5 |
| Alcohol ethoxylate (C11 alcohol, 5EO)[1] | 0.5 | 0.5 | 0.5 |
| Ethoxylated phenol, 4EO[2] | 2.5 | 0 | 0 |
| Glycerin Ethyl | 0 | 0.45 | 0 |

TABLE 5-continued

| Ingredients | Comparative Example E | Example 6A | Example 6B |
|---|---|---|---|
| Ether | | | |
| Glycerin Methyl Ether | 0 | 0 | 2.0 |
| D-limonene | 1.3 | 1.3 | 1.3 |
| Dye | 0.08 | 0.08 | 0.08 |
| Kathon | 0.08 | 0.08 | 0.08 |

[1]TOMODOL ™ 1-5 from Tomah.
[2]Ethylan HB4 from Akzo Nobel Surface Chemistry.

Table 5 illustrates the glycerin short-chain aliphatic ethers as coupling agents in a hard surface cleaner formulation. D-limonene, while not only an expensive ingredient, is very water-insoluble. The D-limonene is solubilized with the aid of a surfactant, ethylan HB4. Similar results were obtained when ethylan HB4 was replaced by glycerin methyl ether or glycerin ethyl ether. Moreover, the coupling is more efficient requiring considerably less coupler compared to the comparative example.

Example 7

Pot and pan cleaner formulations were prepared by mixing together the ingredients in the percentage amounts shown below in Table 6:

TABLE 6

| Ingredients | Comparative Example F | Example 7A | Example 7B |
|---|---|---|---|
| Water, Zeolite softened | 33.5 | 33.5 | 33.5 |
| NaOH 50% | 4.0 | 4.0 | 4.0 |
| Triethanolamine | 4.0 | 4.0 | 4.0 |
| Linear Dodecyl Benzene sulfonic acid 97% | 24.0 | 24.0 | 24.0 |
| Diethanolamide CoCo Amide | 6.0 | 6.0 | 6.0 |
| Nonylphenol ethoxylate | 1.5 | 1.5 | 1.5 |
| Sodium Pareth Ether Sulfate | 11.4 | 11.4 | 11.4 |
| Magnesium Sulfate 27% liquid | 10.8 | 10.8 | 10.8 |
| Propylene Glycol USP | 3.5 | 3.5 | 3.5 |
| Ethanol SDA-3C 190 proof | 1.0 | 0 | 0 |
| Glycerin Ethyl Ether | 0 | 1.0 | 0 |
| Glycerin Methyl Ether | 0 | 0 | 1.0 |
| Distyryl Biphenol Derivative | 0.02 | 0.02 | 0.02 |
| Glutaraldehyde 50% | 0.02 | 0.02 | 0.02 |
| Sozio SZ-4071 Fragrance | 0.3 | 0.3 | 0.3 |
| Dye Pylaklor Blue LX-10092 | 0.0015 | 0.0015 | 0.0015 |

Table 6 demonstrates glycerin short-chain aliphatic ethers as suitable viscosity adjusters in a pot and pan cleaner formulation. The formulation also demonstrates a more green solution: a volatile organic compound (VOC), ethanol SDA-3C, is substituted with a non-VOC compound, glycerin methyl ether or glycerin ethyl ether. The composition, like the comparative example F has a suitable viscosity.

Example 8

Automotive tire treatment formulations were prepared by mixing together the ingredients in the percentage amounts shown below in Table 7:

TABLE 7

| Ingredients | Comparative Example G | Example 8A | Example 8B |
|---|---|---|---|
| Water | 58.92 | 53.92 | 58.92 |
| Cocamidopropyl Betaine 30% | 20.0 | 20.0 | 20.0 |
| Ethylene Glycol Mono Butyl Ether | 10.0 | 0 | 0 |
| Glycerin Ethyl Ether | 0 | 15.0 | 0 |
| Glycerin Methyl Ether | 0 | 0 | 15.0 |
| Propylene Glycol | 2.0 | 2.0 | 2.0 |
| Dicoco Dimethyl Ammonium Chloride | 3.0 | 3.0 | 3.0 |
| Diquaternary Polydimethylsiloxane | 3.0 | 3.0 | 3.0 |
| Acetic Acid | 1.0 | 1.0 | 1.0 |
| Siloxane blend | 2.0 | 2.0 | 2.0 |
| Acid Orange Dye | 0.08 | 0.08 | 0.08 |

Table 7 is yet another example demonstrating glycerin short-chain aliphatic ethers as a coupling agent. Ethylene glycol mono butyl ether, which is a VOC compound, was used as a coupler to aid in solubilizing two very water insoluble compounds, dicoco dimethyl ammonium chloride and diquaternary polydimethylsiloxane. When the non-VOC, glycerin short-chain aliphatic ether replaced the VOC coupling agent, the glycerin short-chain aliphatic ether served to solubilize the two water insoluble components.

Example 9

Paint formulations may be prepared have the following ingredients in the percentage amounts shown below in Table 8:

TABLE 8

| | Comparative Example H | Example 9 |
|---|---|---|
| Grind | | |
| Water | 45.35 | 45.35 |
| Copolymer Dispersant | 15.02 | 15.02 |
| Mineral Oil Defoamer | 3.0 | 3.0 |
| Nano Particle Metal Oxide | 15.0 | 15.0 |
| Ethylene Glycol | 37.0 | 0 |
| Glycerin Ethyl Ether | 0 | 37.0 |
| Amino Alcohol | 0.5 | 0.5 |
| Non-ionic Surfactant | 2.0 | 2.0 |
| Nepheline Syenite | 105.02 | 105.02 |
| Attapulgite Clay | 5.01 | 5.01 |
| Letdown | | |
| 100% Acrylic Primer Vehicle | 410.60 | 410.60 |
| 100% Acrylic Topcoat Vehicle | 86.43 | 86.43 |
| TiO$_2$ Slurry | 294.32 | 294.32 |
| Coalescent | 8.0 | 0 |
| Glycerin Ethyl Ether | 0 | 8.0 |
| Phosphated Co-ester Surfactant | 1.0 | 1.0 |
| Associative RM | 25.0 | 25.0 |
| Non-ionic HEUR RM | 4.0 | 4.0 |
| Opaque Polymer | 50.05 | 50.05 |
| Mildewcide | 6.94 | 6.94 |
| In-can Biocide | 1.0 | 1.0 |

As illustrated in Table 8, the short-chain glycerol ether may be used to replace either the ethylene glycol solvent or the coalescent or both in a paint formulation.

Example 10

Semi-gloss finishes may be prepared having the following ingredients in the percentage amounts shown below in Table 9:

TABLE 9

| Description | Comparative Example I | Example 10 |
|---|---|---|
| Grind | | |
| Water | 73.92 | 73.92 |
| Copolymer Dispersant | 15.02 | 15.02 |
| Mineral Oil Defoamer | 2.00 | 2.00 |
| Zinc Oxide | 5.00 | 5.00 |
| Nano Particle Metal Oxide | 3.0 | 3.0 |
| Ethylene Glycol | 32.0 | 0 |
| Glycerin Ethyl Ether | 0 | 32.0 |
| Amino Alcohol | 0.50 | 0.50 |
| Non-ionic Surfactant | 4.0 | 4.0 |
| Nepheline Syenite | 10.0 | 10.0 |
| Attapulgite Clay | 5.0 | 5.0 |
| Letdown | | |
| 100% Acrylic Primer Vehicle | 410.65 | 410.65 |
| 100% Acrylic Topcoat Vehicle | 86.44 | 86.44 |
| Mineral Oil Defoamer | 3.0 | 3.0 |
| TiO2 Slurry | 297.0 | 297.0 |
| Coalescent | 8.0 | 0 |
| Glycerin Ethyl Ether | 0 | 8.0 |
| Associative RM | 28.0 | 28.0 |
| Non-ionic HEUR RM | 8.0 | 8.0 |
| Opaque Polymer | 58.8 | 58.80 |
| Phosphated Co-ester Surfactant | 1.0 | 1.0 |
| Mildewcide | 6.94 | 6.94 |
| In-can Biocide | 1.0 | 1.0 |

As illustrated in Table 9, the short-chain aliphatic glycerol ether may be used to replace either the ethylene glycol solvent or the coalescent or both in a paint formulation.

Example 11

Adhesive formulations may be prepared having the following ingredients in the percentage amounts shown below in Table 10:

TABLE 10

| Constituents | Comparative Example J | Example 11 |
|---|---|---|
| Epoxy-Novolac ECN 1273 | 25.46 | 25.46 |
| Hexahydrophthalicanhydride | 7.07 | 7.07 |
| Epoxidized cashew nutshell liquid liquid EEW, 250-450 g/eq | 10.73 | 10.73 |
| Epoxy resin EPON 828 | 3.39 | 3.39 |
| Cycloaliphatic epoxy resin CY 184 | 3.10 | 3.10 |
| Melamine formaldehyde CYMEL 303 | 11.95 | 11.95 |
| UV-initiator UVI 6976 | 1.84 | 1.84 |
| Ethyldimethoxyanthracene | 1.32 | 1.32 |
| Glycidoxypropyltrimethoxysilane | 1.09 | 1.09 |
| Fumed silica TS 720 Cab-O-Sil | 1.67 | 1.67 |
| Solvent blue 036 | 0.05 | 0.05 |
| Glycerin Ethyl Ether | 0 | 6.05 |
| PGMEA solvent | 6.05 | 0 |
| Imicure EMI 24 | 0.14 | 0.14 |
| Tetraglycidylmethylenedianiline | 0.14 | 0.14 |

As illustrated in Table 10, the short-chain aliphatic glycerol ether may be used to replace either the PGMEA solvent, coalescent or both in an adhesive formulation.

We claim:

1. A method of reducing viscosity comprising:
   A) preparing a liquid-based laundry, antimicrobial cleaner, or paint composition comprising;
      a) from about 1 wt % to about 50 wt % of one or more surfactants;
      b) from about 2 wt % to about 50 wt % of a glycerin short-chain aliphatic ether solvent; and
      c) water; wherein the glycerin short-chain aliphatic ether solvent replaces a volatile organic compound; and
   B) reducing the viscosity of the composition.

2. The method of claim 1, wherein the glycerin short-chain aliphatic ether is a monoalkyl glycerin aliphatic ether whose alkyl group has 1 to 2 carbon atoms.

3. The method of claim 1, wherein the glycerin short-chain aliphatic ether is glycerin monomethyl ether or glycerin monoethyl ether.

4. A method of coupling or solubilizing otherwise incompatible components comprising:
   A) preparing a liquid-based laundry, antimicrobial cleaner, or paint composition comprising;
      a) from about 1 wt % to about 50 wt % of one or more surfactants;
      b) from about 2 wt % to about 50 wt % of a glycerin short-chain aliphatic ether solvent, wherein the glycerin short-chain aliphatic ether solvent replaces a volatile organic compound; and
   B) coupling or solubilizing otherwise incompatible components into a homogenous, stable aqueous solution.

5. The method of claim 4, wherein the glycerin short-chain aliphatic ether is a monoalkyl glycerin aliphatic ether whose alkyl group has 1 to 2 carbon atoms.

6. A method of reducing viscosity comprising:
   preparing a cleaner composition comprising from about 1 wt % to about 50 wt % of one or more surfactants, from about 2 wt % to about 50 wt % a glycerin short-chain aliphatic ether solvent and water, wherein the glycerin short-chain aliphatic ether solvent replaces a volatile organic compound and wherein the cleaner is a general purpose cleaner, hard surface cleaner, soft surface cleaner, glass cleaner, pot and pan cleaner, automotive cleaner, bathroom and tile cleaner, oven or grill cleaner, toilet cleaner, wood cleaner, sanitizer or floor maintenance cleaner; and
   reducing the viscosity of the composition.

7. The method of claim 1 wherein the volatile organic compound is a glycol ether.

8. The method of claim 1 wherein the volatile organic compound is a specially denatured alcohol.

9. The method of claim 4 wherein the volatile organic compound is a glycol ether.

10. The method of claim 4 wherein the volatile organic compound is a specially denatured alcohol.

11. The method of claim 4 wherein the incompatible component is a d-limonene.

* * * * *